United States Patent [19]

Cochrane

[11] 4,204,529

[45] May 27, 1980

[54] CERVICAL COLLAR APPARATUS

[76] Inventor: William Cochrane, 64 Meadowbrook Cir., Cumming, Iowa 50061

[21] Appl. No.: 866,805

[22] Filed: Jan. 3, 1978

[51] Int. Cl.² ............................................. A61H 1/02
[52] U.S. Cl. ............................... 128/75; 128/DIG. 23
[58] Field of Search ............... 128/75, 76 R, DIG. 23, 128/846, 84 R, 87 B; 297/393; 273/55 R, 55 A; 9/311, 329, 333, 340, 345; 2/415, 2 R

[56] References Cited

U.S. PATENT DOCUMENTS

| | | | |
|---|---|---|---|
| 1,368,937 | 2/1921 | Jordahn | 9/340 |
| 1,759,711 | 5/1930 | Price | 9/340 |
| 1,850,660 | 3/1932 | Coppel | 9/345 |
| 3,657,739 | 4/1972 | Holmes | 2/2 |
| 3,733,631 | 5/1973 | Cohn | 9/340 |
| 3,850,164 | 11/1974 | Hare | 128/75 |
| 4,017,927 | 4/1977 | Massey | 9/340 |
| 4,034,747 | 7/1977 | Leroy | 128/DIG. 23 |
| 4,043,325 | 8/1977 | Ochs et al. | 128/75 |

FOREIGN PATENT DOCUMENTS

| | | | |
|---|---|---|---|
| 448310 | 1/1913 | France | 9/340 |
| 824674 | 2/1938 | France | 9/340 |
| 379445 | 9/1932 | United Kingdom | 9/340 |
| 1122997 | 8/1968 | United Kingdom | 9/340 |

Primary Examiner—Robert W. Michell
Assistant Examiner—Arthur S. Rose
Attorney, Agent, or Firm—McCoy & Morris

[57] ABSTRACT

A cervical collar comprising means adapted to underlie at least the head and trunk of the body of a patient for rigidly supporting a patient and comprising a head supporting portion and a trunk supporting portion, an elongated, elastically deformable core having a mid-portion comprising means for encircling the patient's neck while leaving the front of the neck uncovered, when the cervical collar is in place. The core has a pair of end portions each integral with the mid-portion and extending forwardly from the mid-portion at the front of the patient's neck when the cervical collar is in place. An elongated flexible cover around the core having a pair of end parts each extending longitudinally beyond a respective end portion of the core and means for preventing the longitudinal movement of the cover relative to the core. The trunk supporting portion of said support means comprises means for connecting each of the end parts to the support means and the end parts comprise first tie means for releasably securing each of the end parts to the connecting means and for securing the trunk portion to the support means and for longitudinally lengthening the end portions of the collar to provide mild cervical traction. Second tie means is secured to the cover at a location on the core where one of the end portions is integral with the mid-portion of the core comprising means for tieing together the end portions at a location where the end portions join the mid-portion and at a location spaced from the front of the patient's neck to permit ready access thereto, when the collar is in place.

8 Claims, 3 Drawing Figures

CERVICAL COLLAR APPARATUS

BACKGROUND OF THE INVENTION

This invention relates to a cervical collar apparatus for use in immobilizing and supporting the cervical neck area of a patient. Reference may be made to the following U.S. Pat. Nos.: 3,964,474; 3,530,853; 3,295,516; 3,070,090; and 2,389,690.

There are known cervical collars for supporting and immobilizing the cervical neck area of a patient. For example, see U.S. Pat. No. 3,530,853, wherein several component parts of the collar must be selectively adjusted in order to properly immobilize and support the cervical neck area.

The prior art devices have many disadvantages, especially when used in emergency rescue situations, because of their inherent structural deficiencies. Many of the prior art devices must not only be selectively adjusted to immobilize and support the cervical neck area, but also cannot be applied if the patient is in a prone or supine position without moving the patient's head. In addition, after they are adjusted and applied, none of the prior art devices allow for access to the frontal neck area of the patient. This feature is highly desirable, especially in emergency rescue situations, where easy access to the patient's airway and carotid pulse is required.

Further, none of the prior art devices, when used with emergency rescue spinal immobilization equipment, are able to totally immobilize the patient's neck while at the same time applying comfortable mild cervical traction.

SUMMARY OF THE INVENTION

According to the present invention, a cervical collar apparatus is provided comprising rigid support means adapted to underlie at least the head and trunk of the body of a patient and comprising a head supporting portion and a trunk supporting portion, an elongated, elastically deformable core having a mid-portion comprising means for encircling the back and sides of the patient's neck while leaving the front of the neck uncovered, when the cervical collar is in place. The core has a pair of end portions each integral with the mid-portion and extending forwardly from the mid-portion at the front of the patient's neck when the cervical collar is in place. An elongated cover flexible around the core has a pair of end parts each extending longitudinally beyond a respective end portion of the core. The trunk supporting portion comprises means for connecting each of the end parts to the support means and the end parts comprise first tie means for releasably securing each of the end parts to the connecting means and for securing the trunk portion to the support means and for longitudinally lengthening the end portions to provide mild cervical traction. Means for preventing longitudinal movement of the cover relative to the core is provided and second tie means is secured to the cover at a location on the core where one of the end portions is integral with the mid-portion of the core. The second tie means comprises means for tieing together the end portions at a location where the end portions join the mid-portion, this location being spaced from the front of the patient's neck to permit ready access thereto, when the collar is in place.

The apparatus of the present invention can be part of a total emergency rescue immobilization system for use with a backboard, straps, sandbags and tape. Use of this system totally immobilizes the head and cervical spine of the patient without using direct cervical traction. The apparatus of the present invention is very easy to use and apply since it can be applied and adjusted regardless of the position of the patient, i.e. sitting, prone or supine, and can be used without the necessity of moving the patient's head in any way. In addition, the use of the apparatus of the present invention leaves the patient's airway and carotid pulse readily available for emergency rescue procedures. The apparatus is reusable, lightweight, simple in design, and economical to manufacturer. One size of the apparatus fits all sizes of patients, with the exception of infants and small children. (A smaller apparatus of like design can be used).

Other advantages of the invention will become apparent to those skilled in the art upon reading and understanding the further detailed description of this invention.

DETAILED DESCRIPTION

Figure 2:
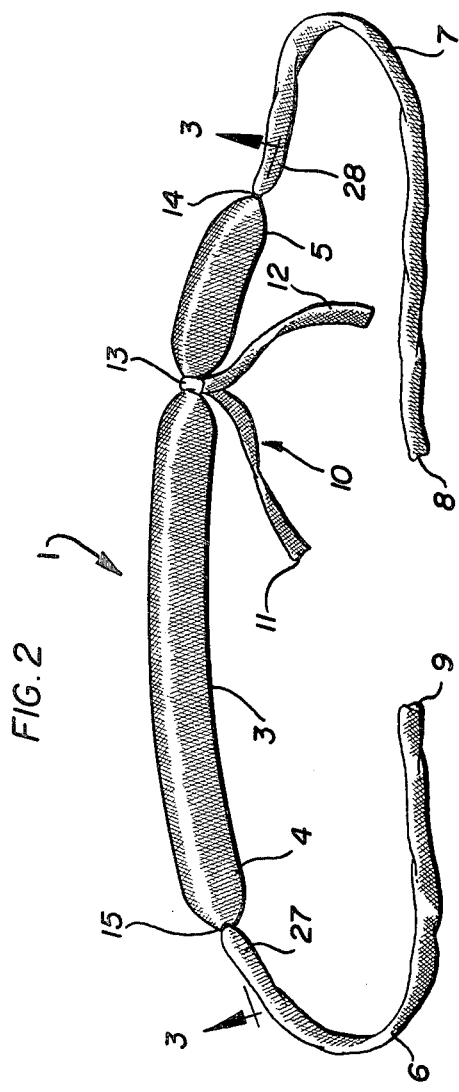
FIG. 2 is a perspective view of the apparatus in an open position.
Figure 1:
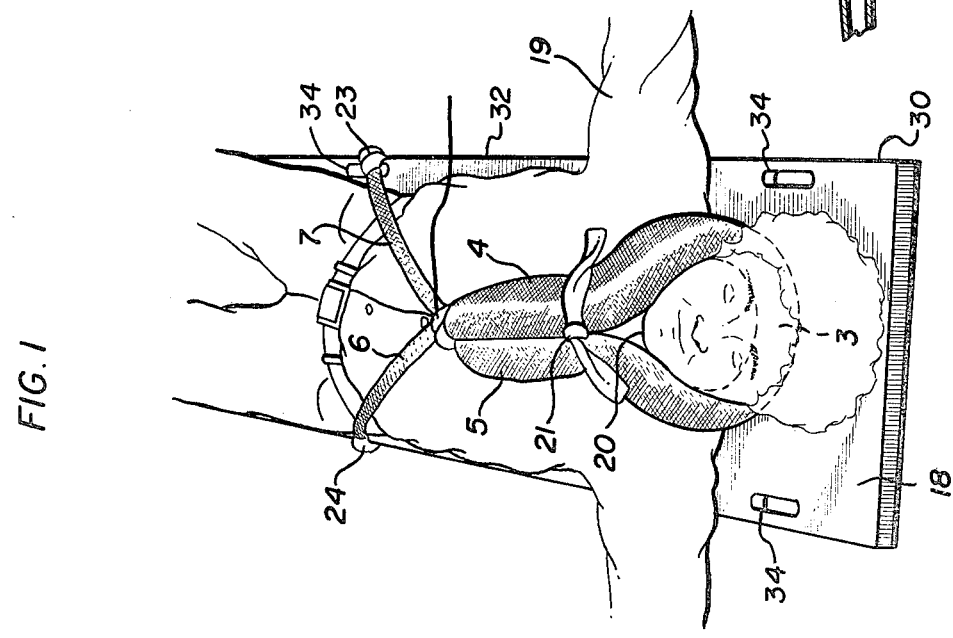
FIG. 1 is a perspective view of the preferred apparatus embodiment of the invention in a closed position as it is actually applied to a patient lying on a backboard.

Referring initially to FIGS. 1-2, the preferred apparatus embodiment of the invention is shown generally at 1 and comprises an elongated, elastically deformable core 2. Core 2 has a midportion 3 which comprises means for encircling the back and sides of patient 19's neck while leaving the front of the neck 20 uncovered when the cervical collar is in place. Core 2 further comprises a pair of end portions, 4 and 5, each integral with midportion 3 and extending forwardly from midportion 3 at the front of patient 19's neck when the cervical collar is in place.

Core 2 is readily commercially available. It is manufactured out of a polyurethane foamed plastic, and preferrably has a rectangular cross-sectional area. Core 2 is approximately 2"×4"×45" and has a density of 1.30 to 1.40 lbs/ft$^3$ and an indent load deflexion of 39 to 40 lbs. It is important to note that the above parameters have been selected to insure the safe operation of the collar, since a collar having a greater density may cut off the blood circulation in the neck, while a collar having a lower density may not give the required cervical support. While a core having a circular or polygonal cross-sectional area may be used, it is preferred that the cross-sectional area be rectangular, since this shape gives maximum support and firmness without sacrificing comfort.

Figure 3:
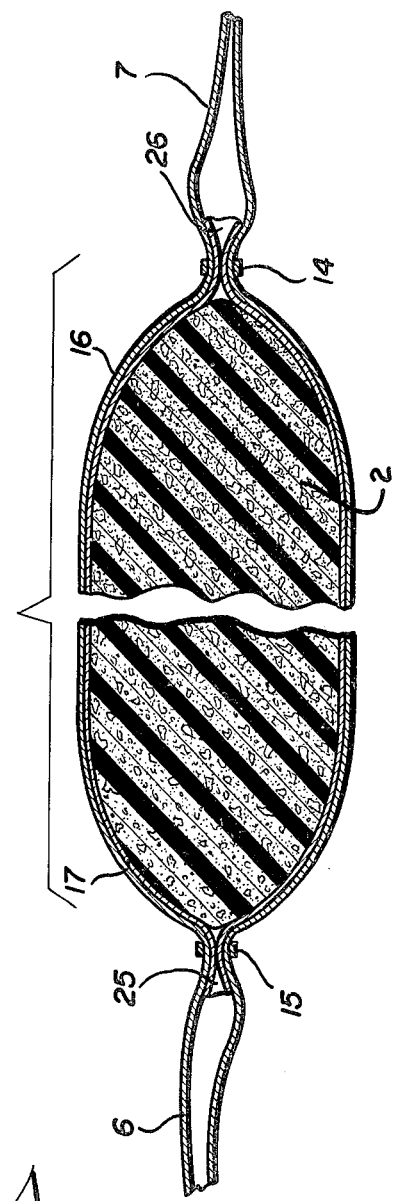
FIG. 3 is a front sectional view along line 3—3 of FIG. 2 showing the layered construction of the apparatus.

The collar apparatus further comprises an elongated, tubular, flexible cloth cover 17, or stockinette (FIG. 3), which is tightly slipped over core 2. Cover 17 has a pair of closed ends 25 and 26 which respectively cover end portions 4 and 5 of core 2 when in place. Cover 17 is approximately 2"×72". The purpose of cover 17 is to round the corners of the rectangular core 2, and to give additional density or firmness to core 2 by slightly compressing it. Cover 17 is commercially available from Johnson & Johnson, and is preferrably made out of a cotton fabric.

A second cover 16 is then tightly slipped over cover 17 and core 2 which are centered within cover 16 leaving loose end parts 6 and 7, each respectively extending longitudinally beyond end portions 4 and 5. As will be shown hereinafter, end parts 6 and 7 are respectively tied to rigid supporting means such as a backboard 18 when the cervical collar is in place to help secure the body of the patient to the backboard and to longitudinally lengthen the end portions of the collar when the collar is in place to provide mild cervical traction. End parts 6 and 7 are approximately 36" long. Backboard 18 comprises a head portion 30 and a trunk portion 32 and has a plurality of openings 34 to releasably secure or tie end parts 8 and 9 thereto.

Cover 16 is also commercially available from Johnson & Johnson and is preferrably made out of a cotton fabric and is 4"×120". It is to be noted that cover 16 also tends to round the rectangular corners of core 2 and to increase its firmness. Although it is not imperative to use cover 17 in the construction of the collar, it is preferred that both covers 16 and 17 be used for optimum product usability.

Once covers 16 and 17 are in place, plastic tieing clips 14 and 15 are positioned and secured adjacent core end portions 4 and 5 and around closed ends 25 and 26 of cover 17 and proximal ends 27 and 28 of loose end parts 6 and 7 for preventing the longitudinal movement of covers 16 and 17 relative to each other and to core 2.

A third stockinette 10 approximately 2"×38" for tieing core end portions 4 and 5 together, is tightly, but releasably secured, at location 13 on core 2 where one of end portions 4 or 5 is integral with mid-portion 3 of core 2 (approximately 10" from either end of the core). Tieing stockinette 10 to core 2 leaves two dangling ends 11 and 12 wherein one of the dangling ends 12 is preferrably longer than the other dangling end 11. These dangling ends encircle both end portions 4 and 5 of core 2 when the collar is in place around the patient's neck (see FIG. 1). In addition, each dangling end is tied to the other dangling end in a knot when either dangling end 11 or 12 has encircled both end portions 4 and 5 of core 2 thereby joining together end portions 4 and 5 at a location 13 where the end portions 4 and 5 join mid-portion 3. Location 13 is spaced from the front of the patient's neck to permit ready access thereto, when the collar is in place.

The collar apparatus of the present invention can be applied to a patient whether the patient is sitting, prone or supine and without the patient having to move his head. It is obvious that this feature is highly desirable in emergency rescue situations since it is not desirable to move the head of a patient suspected of sustaining a cervical injury. For example, in the most difficult position, that is, supine, dangling end 6 or 7 is passed behind the patient's neck until either end portion 4 or 5 of core 2 is adjacent the side of the patient's head. The collar is then compressed by hand by the rescuer and passed behind the patient's neck until it is centered behind the head. After the collar is centered, the rescuer releases his hand to allow the deformable foamed core to expend to its natural shape behind the neck area of the patient. End portions 4 and 5 are then placed together and stockinette 10 is tied around both end portions by using a conventional knot 21, leaving open space 20 in the front of the patient's neck. Opening 20 leaves the patient's airway and carotid pulse readily available for emergency rescue procedures. For example, the collar can remain in place for endotracheal intubation and/or placement of an esophageal obdurator airway.

Loose ends 6 and 7 of stockinette cover 16 are preferrably twisted together twice at 22 just at ends 27 and 28 and at the appropriate time during the rescue operation, ends 8 and 9 are tied to backboard 18 at 23 and 24. If the apparatus of the present invention is used in conjunction with straps, sandbags and tape to totally immobilize the patient's head and cervical area, the tightening of ends 8 and 9 at 23 and 24 applies an even amount of very mild traction to the cervical vertabrae, thereby making it virtually impossible for the patient's cervical area to be damaged by movement of the patient.

It is to be noted that use of the apparatus of the present invention aids in the comfort to the patient since there is no "choking" sensation that customarily is felt with conventional cervical collar apparatus. The size of the apparatus of the present invention is intended to fit an adult. The dimensions of the apparatus may be appropriately redesigned to accommodate children and infants.

What is claimed is:

1. A cervical collar apparatus comprising:

means adapted to underlie at least the head and trunk of the body of a patient for rigidly supporting a patient;

said support means comprising a head supporting portion and a trunk supporting portion;

an elongated, elastically deformable core;

said core having a mid-portion comprising means for contiguously encircling a patient's neck while leaving the front portion of the neck uncovered when said cervical collar is in place;

said core having a pair of end portions each integral with said mid-portion and extending forwardly from said mid-portion at the front of a patient's neck when said cervical collar is in place;

an elongated, flexible cover around said core;

said cover having a pair of end parts each extending longitudinally beyond a respective end portion of the core;

said trunk supporting portion of said support means having means for connecting each of said end parts thereto;

said end parts comprising first tie means for releasably securing each of said end parts to said connecting means and for securing the trunk portion to said support means and for longitudinally lengthening said end portions of said collar when said collar is in place to provide mild cervical traction;

means for preventing the longitudinal movement of said cover relative to said core;

second tie means secured to said cover at a location on said core where one of the end portions is integral with the mid-portion of the core; and, said second tie means comprising means for tieing together said end portions at a location where said end portions join said mid-portion, said location being spaced from the front of the neck, to permit ready access thereto, when said collar is in place.

2. A cervical collar as recited in claim 1 wherein said second tie means comprises:

an elongated, flexible member tied around said cover and said core at a location on said core where one of the end portions is integral with the midportion of said core to secure the member thereto;

said member having a pair of dangling ends;

each of said dangling ends comprising means for tieing one dangling end to the other dangling end at a location where said end portions join said mid-portion when said dangling ends have encircled the other core end portion; and, said location being spaced from the front portion of the neck, to permit ready access thereto, when said collar is in place.

3. A cervical collar as recited in claim 1 wherein said core comprises a foamed plastic material.

4. A cervical collar as recited in claim 3 wherein: said core has a density range of 1.30 to 1.40 lbs/ft$^3$ and an indent load deflection range of 39 to 49 lbs.

5. A cervical collar as recited in claim 1 wherein: said core has a rectangular cross-sectional area.

6. A cervical collar as recited in claim 5 wherein: said cover comprises means for rounding off the corners of said rectangular cross-section area of said core and for making said core firmer.

7. A cervical collar as recited in claim 6 and comprising:

a second elongated cover tightly enclosing said core between the core and said first recited cover;

said additional cover having a pair of closed ends each located adjacent a respective end portion of said core.

8. A cervical collar as recited in claim 7 wherein said additional cover comprises means for rounding off the corners of said rectangular cross-sectional area of said core and for making said core firmer.

* * * * *